US009783623B2

(12) United States Patent
Durot et al.

(10) Patent No.: US 9,783,623 B2
(45) Date of Patent: *Oct. 10, 2017

(54) POLYMERISABLE PLASTICISER, LIQUID POLYURETHANE RESIN COMPOSITION COMPRISING SAME AND USES THEREOF

(71) Applicant: SOPREMA, Strasbourg (FR)

(72) Inventors: Louis Durot, Paris (FR); Pierre-Etienne Bindschedler, Obernai (FR); Virginie Francois Barseghian, Paris (FR); Remi Perrin, Boersch (FR)

(73) Assignee: Soprema, Strasbourg (FR)

( * ) Notice: Subject to any disclaimer, the term of this patent is extended or adjusted under 35 U.S.C. 154(b) by 158 days.

This patent is subject to a terminal disclaimer.

(21) Appl. No.: 14/352,021

(22) PCT Filed: Oct. 18, 2012

(86) PCT No.: PCT/FR2012/052369
§ 371 (c)(1),
(2) Date: Apr. 15, 2014

(87) PCT Pub. No.: WO2013/057429
PCT Pub. Date: Apr. 25, 2013

(65) Prior Publication Data
US 2014/0249263 A1 Sep. 4, 2014

(30) Foreign Application Priority Data
Oct. 20, 2011 (FR) ...................................... 11 59493

(51) Int. Cl.
C07C 271/06 (2006.01)
C07C 271/32 (2006.01)
C07C 271/40 (2006.01)
C08F 8/30 (2006.01)
C08G 18/28 (2006.01)
C08G 18/64 (2006.01)
C08G 18/76 (2006.01)
C08G 18/78 (2006.01)
C08G 18/79 (2006.01)
C08G 18/80 (2006.01)
C08L 95/00 (2006.01)
C09D 175/08 (2006.01)
C09D 195/00 (2006.01)

(52) U.S. Cl.
CPC .............. C08F 8/30 (2013.01); C07C 271/06 (2013.01); C07C 271/32 (2013.01); C07C 271/40 (2013.01); C08G 18/2825 (2013.01); C08G 18/6476 (2013.01); C08G 18/7664 (2013.01); C08G 18/7843 (2013.01); C08G 18/791 (2013.01); C08G 18/8067 (2013.01); C09D 175/08 (2013.01); C08F 2810/40 (2013.01); C08L 95/00 (2013.01); C09D 195/00 (2013.01)

(58) Field of Classification Search
CPC ...... C08F 8/30; C08F 2810/40; C07C 271/06; C07C 271/32; C07C 271/40; C08G 18/2825; C08G 18/6476; C08G 18/7664; C08G 18/7843; C08G 18/791; C08G 18/8067; C08L 95/00; C09D 175/08; C09D 195/00
See application file for complete search history.

(56) References Cited

U.S. PATENT DOCUMENTS

| 4,355,138 | A | * | 10/1982 | Markusch | .......... | C08G 18/8064 525/127 |
|---|---|---|---|---|---|---|
| 4,795,760 | A | | 1/1989 | Lucke | | |
| 4,871,792 | A | | 10/1989 | Lucke | | |
| 5,219,979 | A | | 6/1993 | Greco | | |
| 5,319,008 | A | | 6/1994 | Janoski | | |
| 5,369,207 | A | | 11/1994 | Wolff et al. | | |
| 6,060,574 | A | | 5/2000 | Schmalstieg et al. | | |
| 2003/0022965 | A1 | | 1/2003 | Durot et al. | | |
| 2003/0134127 | A1 | | 7/2003 | Konig et al. | | |
| 2010/0105829 | A1 | | 4/2010 | Schmatloch | | |
| 2010/0152381 | A1 | | 6/2010 | Savino et al. | | |
| 2014/0275359 | A1 | * | 9/2014 | Durot | .................. | C08G 18/289 524/68 |

FOREIGN PATENT DOCUMENTS

| AU | 20324/88 | 2/1990 |
|---|---|---|
| EP | 1 108 735 A1 | 6/2001 |
| EP | 1 798 248 A1 | 6/2007 |
| EP | 2 383 304 A1 | 11/2011 |
| GB | 2 242 435 A | 10/1991 |
| WO | 02/051901 A1 | 7/2002 |
| WO | 2010/106022 A1 | 9/2010 |

OTHER PUBLICATIONS

Carter, N. G. "Oxazolidine Diluents: Reacting for the environment", Surface Coatings International (2009), vol. 82(10), pp. 497-502.
The International Search Report for PCT/FR2012/052369 dated May 3, 2013.

* cited by examiner

Primary Examiner — Patrick Niland
(74) Attorney, Agent, or Firm — McDonnell Boehnen Hulbert & Berghoff

(57) ABSTRACT

The present invention relates to a polymerisable plasticiser formed by a hydrocarbon chain, one end of which bears more than one isocyanate function, said hydrocarbon chain comprising and/or being substituted by an aromatic ring and/or an aliphatic ring and/or said hydrocarbon chain is substituted by at least two hydrocarbon chains that can comprise an unsaturation, and the number of isocyanate functions being strictly greater than 1, preferably greater than 1.2, and, more preferably, grater than 1.5 but less than or equal to 2.2. The invention also relates to liquid polyurethane resin compositions and, in particular, stable, ready-to-use liquid polyurethane resin compositions comprising said plasticiser. The invention further relates to methods for replacing all or part of the exogenous plasticiser and/or solvent in a polyurethane resin by adding said polymerisable plasticiser.

18 Claims, No Drawings

POLYMERISABLE PLASTICISER, LIQUID POLYURETHANE RESIN COMPOSITION COMPRISING SAME AND USES THEREOF

This application is a U.S. national phase of International Application No. PCT/FR2012/052369, filed Oct. 18, 2012, the disclosure of which is hereby incorporated by reference in its entirety.

FIELD OF APPLICATION

The present invention relates to a low-viscosity polymerizable plasticizer, with high diluent power, which makes it possible to lower or eliminate the solvent content in liquid polyurethane resin or bituminous polyurethane resin compositions, while at the same time reducing or eliminating the drawbacks associated with the use of exogenous plasticizers (weakening of the mechanical strength, of the resistance to aging, of the adhesion, weakening of the water resistance, etc.).

In addition, said polymerizable plasticizer makes it possible to improve the compatibility with hydrocarbon fillers in liquid polyurethane resin or bituminous polyurethane resin compositions intended to be applied as a thin layer to form a coating.

PRIOR ART

Plasticizers are frequently used in polyurethane resin compositions, especially in one-component polyurethane resin compositions, for raising the solids content, lowering the viscosity, reducing the bubbling and, where possible, lowering the production cost. Furthermore, in composite polymer compositions, especially such as bituminous polyurethane resin compositions, aromatic plasticizing oils and plasticizers such as diisopropylnaphthalene, dioctyl phthalate (DOP), diisononyl phthalate (DINP), Mesamoll®, trimethylpentanediol diisobutyrate (TXIB) and butylbenzyl phthalate, act as a compatibilizer, which makes it possible to have a homogeneous and stable composition.

Conventionally, plasticizers are exogenous and inert, i.e. they do not react with themselves or with polymers. On the other hand, during their addition, known as plasticization, exogenous plasticizers separate the polymer chains, thus reducing the interactions between the chains. However, inert exogenous plasticizers have certain defects since they have an influence on the final coating. Specifically, the plasticizer separates the polymer chains, which leads to a final coating that has weakened mechanical and aging properties. Furthermore, the separation of the polymer chains will give a coating that is capable of absorbing water, which will be reflected by swelling of the coating and, in the long term, a lack of adhesion thereof. Now, if it is desired to obtain a waterproof coating, said coating must not have any adhesion defects or substantial water absorption. What is more, the use of an inert exogenous plasticizer does not make it possible to obtain enough adhesiveness to ensure a sufficiently intimate, strong and long-lasting attachment on different supports such as bitumen or cement, especially on rough or vertical supports, and even on horizontal supports with stagnant water without primer.

It is thus often necessary, in order to use these compositions comprising an exogeneous plasticizer, to envisage an adhesion primer and/or an additional specific protective layer.

Bayer has disclosed, in patent EP 1 108 735, a solvent-free two-component non-bituminous polyurethane resin composition. The liquid state of the composition is obtained by using a plasticizer which does not comprise any isocyanate functions NCO or any hydroxyl functions (—OH), i.e. it is not polymerizable. However, due to the massive use of this exogenous plasticizer, the final coating has reduced mechanical properties, increased UV sensitivity and sensitivity to fungal parasites, such as molds and fungi.

An important application of polyurethane coatings is exterior use. When a colored coating is desired on a traffic-bearing zone, a bitumen-free polyurethane resin composition, or non-bituminous polyurethane resin, which has high mechanical strength is used. On the other hand, when it is desired to make a coating on a non-traffic-bearing zone, especially on a roof, a polyurethane resin composition with bitumen, or bituminous polyurethane resin, which shows high adhesion on a bituminous support or on a concrete support free of primer may be used. The introduction of bituminous mixtures makes it possible to lower the price of the composition and to improve the adhesion to a bituminous support, but it is a source of additional difficulties associated with the compatibilization of bitumen with the most commonly used polar polyurethane resins or polar polyurethane prepolymers.

At the present time, the only compositions found on the market are solvent-free two-component bituminous polyurethane resin compositions or alternatively solvent-bearing one-component bituminous polyurethane resin compositions which incorporate large amounts of exogenous plasticizers, usually in the form of aromatic oils, and/or of liquid filler or liquid diluent. However, the coatings obtained with such products cannot be applied to a bituminous support. Indeed, the aromatic oil exudes, dilutes the support, and a liquid layer forms between the bitumen of the support and the bitumen of the waterproof coating. Thus, such a coating is unsuitable for repairing an existing bituminous coating. Furthermore, the prior art one-component bituminous polyurethane resin compositions cannot be used externally. Indeed, after application, the plasticizing oil evaporates, giving rise, in a relatively short period of time, to microfissures in the coating, which weaken the waterproof properties. Such bituminous polyurethane resins using a plasticizing aromatic oil as compatibilizer are the usual and customary products on the market, which cannot be used without protection or on bituminous supports, and which are used only on concrete or cement supports with protection.

In addition to the previously mentioned problems, the products described under the name "Tremco system" in U.S. Pat. No. 5,319,008 have viscosities between 40,000 and 75,000 centipoises. They are therefore products that must be heated before application, commonly known as "hot-melt" products, since they are not liquid at room temperature or not sufficiently liquid at room temperature to be able to be applied easily. These products are therefore not commercially viable.

In patent application FR 2 787 801, Applicant has disclosed a stable, ready-to-use liquid bituminous polyurethane resin composition. This composition is suitable for waterproofing self-protected exterior surfaces. However, in order to be industrially usable, this composition must contain a solvent. Solvents, however, are undesirable and expensive and, due to ecological and public health reasons, their use is gradually being reduced and will in all likelihood be banned within a few years.

Teroson has disclosed, in U.S. Pat. No. 4,871,792, a solvent-free ready-to-use bituminous polyurethane resin composition. The compatibilization between the bitumen and the prepolymer is achieved by using two plasticizers: a butylurethane-formaldehyde-carbamate resin and 2,3-dibenzyltoluene. The drawback of this composition is that it generates toxic formaldehyde, which implies specific toxicity labeling that dissuades the consumer. Furthermore, the composition has a pasty rather than liquid consistency, which renders it fit for use as a mastic and not as a liquid waterproof coating that can be applied without heating. Since mastic is very thick, it does not need to have good resistance to aging since only a small area is exposed. Such a composition, applied as a coating in a thickness of 1 to 3 mm, would not have sufficient resistance in an external medium and could not be applied without heating.

Tremco has disclosed, in patent application GB 2 242 435, a solvent-free bituminous polyurethane resin composition. The semiliquid state of the composition is due to the use of a surfactant type molecule having a semipolar head and an aliphatic chain. This surfactant is a good compatibilizer which disperses the bitumen in the prepolymer. However, this surfactant is not a plasticizer; a plasticizer must thus necessarily also be added to the composition in order to obtain a liquid composition. Since the described composition does not contain any solvent, the exogenous plasticizer, being non-polymerizable, cannot remain in the final coating, and substantial exudation is observed after application.

The present inventors have found that it is possible to overcome all the drawbacks associated with the use of a plasticizer and/or compatibilizer in compositions and products of the prior art while at the same time limiting, or even eliminating, the use of a solvent, by using a polymerizable plasticizer that does not remain in the composition in its free form after its application and that allows bitumens to be compatiblized with prepolymers.

The polymerizable plasticizer according to the invention makes it possible to lower the viscosity of the polyurethane resin compositions, preferably of the one-component polyurethane resin compositions, thereby making it possible to obtain low-viscosity liquid compositions that can be easily applied by users with a spatula, roller or brush.

Moreover, the polymerizable plasticizer according to the invention makes it possible to reduce, or even eliminate, the use of a solvent in polyurethane resin compositions, preferably one-component polyurethane resin compositions, which limits, or even eliminates, the drawbacks associated with the presence of solvents and especially:

an unpleasant odor due to the volatile organic compounds,
a toxicity that results in specific labeling,
problems with regard to environmental regulations.

Also, the Applicant has observed that the coatings obtained with solvent-free non-bituminous polyurethane resin compositions which comprise the polymerizable plasticizer adhere better to certain supports than the coatings obtained with compositions with solvent but without any polymerizable plasticizer. This enhanced adhesion makes it possible to apply the compositions directly onto concrete, without the need to apply an adhesion primer layer beforehand.

What is more, the polymerizable plasticizer according to the invention makes it possible to improve the compatibility between the bituminous fillers and the prepolymers in bituminous polyurethane resin compositions, which are preferably one-component, which makes it possible to reduce, or even eliminate, the use of standard compatibilizers such as exogenous plasticizers in bituminous polyurethane resin compositions. Thus, the coatings obtained with the polymerizable plasticizers according to the invention do not have the following drawbacks associated with the use of standard exogenous plasticizers:

weakening of the mechanical strength,
weakening of the adhesion,
reduced aging over time,
increased water absorption.

Moreover, replacing exogenous plasticizers with the polymerizable plasticizer in bituminous polyurethane resin compositions eliminates the exudation of said exogenous plasticizers, which makes it possible to apply the bituminous compositions directly onto bitumen, whereas the bituminous compositions which comprise exogenous plasticizers can only be applied to concrete or cement supports and may additionally require the application of a protective layer over the bituminous coating.

Thus, the present invention relates to a polymerizable plasticizer, to liquid polyurethane resin compositions, preferably stable one-component liquid polyurethane resin compositions, containing it and to the use thereof for making waterproof coatings or protective coatings wherein said plasticizer is no longer in its free form but is polymerized.

The coatings obtained have good mechanical strength, are resistant to UV, to oxidation aging, to water and to chemical attack and do not have any surface defects nor any adhesion defect (bubbles, swelling or exudation). Such coatings may be traffic-bearing and are particularly suitable for use in an unprotected external medium as waterproof coatings.

Definitions

According to the present invention, the term "liquid composition" means a composition with a viscosity between 1,000 and 40,000 centipoises, said viscosity being measured at 23° C. using a Brookfield viscometer (for viscosities of less than 10,000 centipoises, the measurements are taken with the R5 module at a speed of 30 rpm and for viscosities of greater than 10,000 centipoises, the measurements are taken with the R6 module at a speed of 20 rpm). Such a viscosity allows the application of the composition especially with a roller commonly known as a pile roller or a brush to form 0.5 to 2 mm thick layers in one or more applications.

The term "one-component composition or ready-to-use composition" means a composition which is intended to be applied on its own by the final user, i.e. by the worker who will perform the waterproof coating. Such a ready-to-use composition is conventionally known in the art as a "one-component" composition, as opposed to compositions which require the addition of a catalyst or hardener or other reactive agent before use or which must be applied in a limited time span (a few hours) after being mixed.

The term "stable composition" means a composition which can be stored for a minimum of 4 months without any phase separation or solification being observed.

The term "traffic-bearing coating" means a coating whose mechanical strength is sufficient to allow the circulation of people and vehicles on its free surface.

The term "coating with good mechanical strength" means a coating which has a tensile strength of greater than or equal to 2 MPa for a non-traffic-bearing coating and a tensile strength of greater than or equal to 5 MPa for a traffic-bearing coating (the tensile strength is measured on an Instron machine according to standard EN ISO 527-3). Conventionally, in practice, for an elongation of greater than 100%, a non-traffic-bearing coating has a tensile strength of 2 to 3 MPa and a traffic-bearing coating has a tensile strength of 5 to 8 MPa. Higher values for a traffic-bearing coating are obviously acceptable.

The term "prepolymer" means the reaction product of a polyol or of a polyol mixture containing a number of OH functions between 1.5 and 3 and a molecular weight between 900 and 3,000 g/mol, preferably between 1,000 and 2,800 g/mol and more preferentially between 1,500 and 2,500 g/mol with a polyisocyanate or a mixture of polyisocyanates containing a number of NCO functions between 1.6 and 3; in a ratio such that the number of NCO functions of the polyisocyanate or of the polyisocyanate mixture relative to the number of OH functions of the polyol or of the polyol mixture is from 1.5 to 2.5 approximately.

The term "polyisocyanate" means a compound containing more than one isocyanate function, diisocyanate may therefore also be termed in the present application a polyisocyanate.

The term "TDI" means toluene diisocyanate.

The term "MDI" means diphenylmethane diisocyanate.

The term "HDI" means hexamethylene diisocyanate.

The term "IPDI" means isophorone diisocyanate.

The term "—OH number of the molecule [A]" means the number of OH groups present on the molecule [A].

The term "hydroxyl number of [A]" means the total number of reactive hydroxyl groups on [A], as can be measured by back-titration with potassium hydroxide. The hydroxyl number is expressed in mg KOH/g, which corresponds to the amount of KOH in mg which is required to neutralize 1 g of [A].

The term "solvent" means any solvent that is conventionally used in polyurethane resin compositions, said solvent being inert toward the reagents contained in the composition, liquid at room temperature and having a boiling point below 240° C.

The term "exogenous plasticizer" means a molecule or oligomer added to the polymer resin compositions, such as a polyurethane resin composition, to make the resulting material more flexible, less resistant, more resilient and/or easier to manipulate, said exogenous plasticizer being inert, i.e. it does not comprise any reactive functions that would enable it to react with itself or with the prepolymers contained in the composition.

The term "alkyl" means a hydrocarbon radical containing 1 to 10 carbon atoms, corresponding to general formula $C_nH_{2n+1}$ wherein n is greater than or equal to 1. The alkyl groups may be linear or branched and may be substituted with the groups indicated in the present patent application.

The term "aryl" means a polyunsaturated aromatic hydrocarbon group containing only one ring (i.e. phenyl) or several fused rings (for example naphthyl) or several rings linked via a covalent bond (for example biphenyl), which typically contain 5 to 12 and preferentially 6 to 10 carbon atoms, and wherein at least one ring is aromatic. The aromatic ring may optionally comprise one to two additional fused rings (i.e. cycloalkyl, heterocycloalkyl or heteroaryl). The term "aryl" also comprises partially hydrogenated derivatives of the carbocyclic system described above.

When the suffixes "ene" or "diyl" are used in conjunction with an alkyl group, this means that the alkyl group defined above contains two single bonds as points of attachment to other groups.

The term "arylalkyl" or "heteroarylalkyl" means a linear or branched alkyl substituent containing a carbon atom attached to an aryl or heteroaryl ring.

The term "heteroaryl" means one ring or two rings that are fused or linked via a covalent bond, comprising 5 to 12 carbon atoms and preferentially 6 to 10 carbon atoms, wherein at least one of the rings is aromatic and wherein at least one or more carbon atoms are replaced with oxygen, nitrogen and/or sulfur. The term "heteroaryl" also comprises systems described above containing a fused aryl, cycloalkyl, heteroaryl or heterocycloalkyl group.

The term "cycloalkyl" means a saturated or unsaturated, cyclic monovalent hydrocarbon, containing one or two rings and comprising 3 to 10 carbon atoms.

The term "heterocycloalkyl" means a cycloalkyl wherein at least one carbon atom is replaced with an oxygen, nitrogen and/or sulfur atom.

The term "arylcycloalkyl" or "heteroarylcycloalkyl" means a cycloalkyl that is fused or linked via a covalent bond to an aryl or heteroaryl ring.

The term "arylheterocycloalkyl" or "heteroarylheterocycloalkyl" means a heterocycloalkyl that is fused or linked via a covalent bond to an aryl or heteroaryl ring.

The term "monounsaturated or polyunsaturated hydrocarbyl" means a hydrocarbon chain containing 2 to 30 carbon atoms which may comprise at least one unsaturation.

The following groups: alkyl, aryl, arylalkyl, arylcycloalkyl, arylheterocycloalkyl, heteroaryl, heteroarylalkyl, hydrocarbon with at least one unsaturation, monounsaturated or polyunsaturated hydrocarbon chain, may also comprise one or more standard substituents chosen from: halogen, alkyl, cycloalkyl, heterocycloalkyl, aryl, heteroaryl, alkoxy, haloalkyl, arylalkyl, heteroarylalkyl, arylheterocycloalkyl.

Polymerizable Plasticizer

A first object of the invention is a polymerizable plasticizer containing a hydrocarbon chain, only one end of which bears more than one isocyanate function, said hydrocarbon chain comprising and/or being substituted with an aromatic ring and/or an aliphatic ring and/or said hydrocarbon chain being substituted with at least two hydrocarbon chains that may comprise an unsaturation, and the number of isocyanate functions being strictly greater than 1, preferably greater than 1.2, more preferentially greater than 1.5 and less than or equal to 2.2.

The hydrocarbon chain, of which only one end bears more than one isocyanate function, must not be a purely aliphatic unsubstituted chain, in order for the polymerizable plasticizer according to the invention to have sufficient diluent power to replace some or all of the solvent of a liquid polyurethane resin composition.

Preferably, the two hydrocarbon chains that may comprise an unsaturation, which may substitute the hydrocarbon chain, of which only one end bears more than one isocyanate function, do not comprise any oxygen atoms, and preferably do not comprise any atoms other than carbon and hydrogen.

The number of isocyanate functions is estimated by calculation after NCO titration by back-titrating the excess of dibutylamine with hydrochloric acid (according to standard EN ISO 14896-2006).

The polymerizable plasticizer according to the invention has a molecular weight between 600 and 3,000 g/mol, preferably between 700 and 2,500 g/mol and even more preferentially between 800 and 2,000 g/mol.

The polymerizable plasticizer according to the invention should have a viscosity that is as low as possible, it being understood that it must be introduced into liquid compositions with a limited solvent content, or even into solvent-free compositions. An acceptable viscosity is between 400 and 14 000 centipoises, preferably between 1,300 and 13,000 centipoises and even more preferentially between 2,000 and 12,000 centipoises, measured with a Brookfield viscometer (spindle 6, speed 20 rpm, 25° C.). In the case of a plasticizer prepared based on aliphatic polyisocyanate, the viscosity will be of the order of 5,000 to 14,000 centipoises, whereas in the case of a plasticizer prepared based on aromatic polyisocyanate, the viscosity will be lower, of the order of 400 to 4,000 centipoises. The diluent power and the low viscosity of the polymerizable plasticizer are due to the presence of a hydrocarbon chain that is not a purely aliphatic unsubstituted chain and to the number of isocyanate functions of less than or equal to 2.2 present at only one end. Specifically, if the polymerizable plasticizer comprised isocyanate functions at more than one end, the viscosity would be too high for it to be able to be used as a diluent in replacement for all or part of the solvent contained in a liquid polyurethane resin composition. In addition, this product is a good compatibilizer for prepolymers with bituminous mixtures using natural or synthetic bitumens by virtue of its hydrocarbon chain bearing or substituted with an aromatic ring and/or an aliphatic ring and/or by virtue of its hydrocarbon chain substituted with at least two hydrocarbon chains that may comprise an unsaturation.

The polymerizable plasticizer object of the invention is intended to be introduced in liquid polyurethane resin or bituminous polyurethane resin compositions, preferably stable one-component compositions, which also contain prepolymers. After application of the composition onto a surface, the polymerizable plasticizer polymerizes with these prepolymers. In contrast with a standard plasticizer which can exude on aging after application, the polymerizable plasticizer according to the invention will not exude since it is no longer in its free form in the final coating. The defects associated with this exudation, such as the reduction of the adhesion to the support and of the mechanical performance qualities, water absorption, poor resistance to aging, increased sensitivity to UV and to fungal parasites, and the appearance of bubbles and blisters on the coating, will thus be avoided by the use of the polymerizable plasticizer according to the invention.

According to a particular embodiment, the polymerizable plasticizer has general formula (I) below:

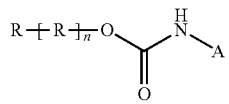

(I)

wherein each R independently represents a unit which does not comprise any hydroxyl functions or any isocyanate functions and which is chosen from the group comprising:
  alkyl,
  cycloalkyl,
  aryl,
  heteroaryl,
  arylcycloalkyl,
  arylheterocycloalkyl,
  heteroarylalkyl,
  heteroarylcycloalkyl,
  monounsaturated or polyunsaturated hydrocarbyl;
and wherein n is between 2 and 50, preferably between 3 and 30 and even more preferentially between 5 and 25;
and wherein A is a group comprising a number of isocyanate functions strictly greater than 1, preferably greater than 1.2, more preferentially greater than 1.5 and less than or equal to 2.2;
on condition that formula (I) comprises either at least one aromatic or aliphatic ring in at least one unit R or at least two alkyl units R substituted with an alkyl chain.
  Preferably, the "group" of A is:
    a polymer chain (originating from a polymeric MDI) corresponding to formula (A1):

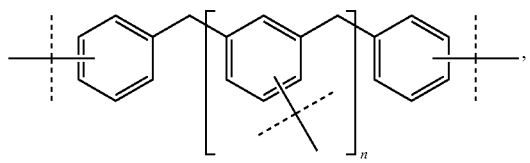

(A1)

a radical corresponding to formula (A2) or to a related radical of a TDI trimer:

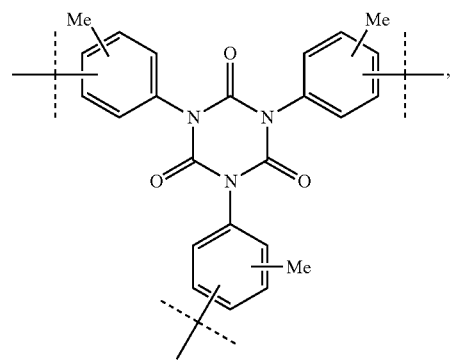

(A2)

a radical corresponding to one of the formulae (A3) and/or (A4) or to a related radical of a HDI trimer:

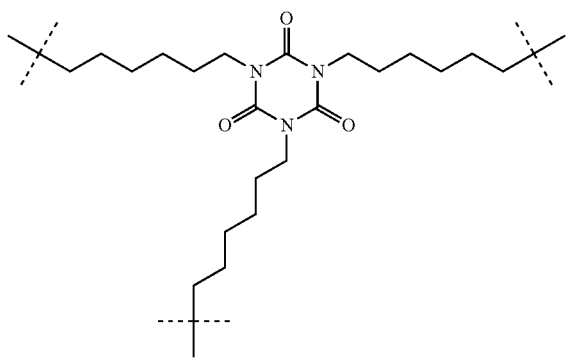

(A3)

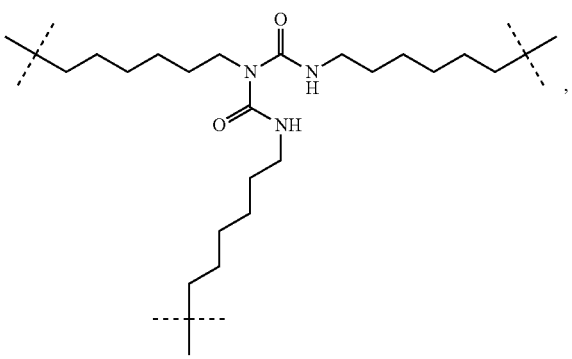

(A4)

a radical corresponding to formula (A5) or to a related radical of an IPDI trimer:

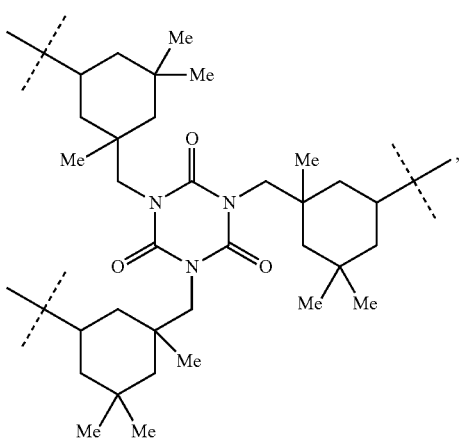

(A5)

wherein each dashed line represents a point of attachment to a NCO function or to the group —NHCOO—(R)$_n$—R of formula (I) of the polymerizable plasticizer and on condition that there is at least one dashed line that is a point of attachment to said group —NHCOO—(R)$_n$—R and that the remaining lines represent a point of attachment to a NCO function.

According to a preferential embodiment, the polymerizable plasticizer has general formula (II) below:

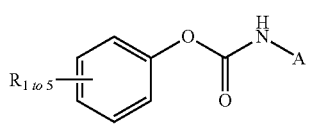

(II)

wherein the substituents R$_{1\ to\ 5}$ are each independently:
halogen,
alkyl,
haloalkyl,
cycloalkyl,
aryl,
alkoxy,
arylalkyl,
heteroaryl,
monounsaturated or polyunsaturated hydrocarbon chain;
and wherein R$_{1\ to\ 5}$ do not contain any hydroxyl functions or any isocyanate functions;
and wherein at least one from among R$_{1\ to\ 5}$ represents a hydrocarbon polymer chain comprising and/or being substituted with at least one repeating unit:
alkyl,
aryl,
arylalkyl,
arylcycloalkyl,
arylheterocycloalkyl,
heteroaryl,
heteroarylalkyl,
heteroarylcycloalkyl,
heteroarylheterocycloalkyl,
hydrocarbyl with at least one unsaturation;
and wherein A is a group comprising a number of isocyanate functions strictly greater than 1, preferably greater than 1.2, more preferentially greater than 1.5 and less than or equal to 2.2.

According to a particular embodiment, the polymerizable plasticizer has general formula (II), wherein the hydrocarbon polymer chain corresponds to general formula (IIIa) wherein Z is a carbon and/or oxygen atom and n is between 2 and 50, preferably between 3 and 30 and even more preferentially between 5 and 25.

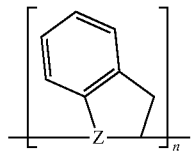

(IIIa)

According to a particular embodiment, the polymerizable plasticizer has general formula (II), wherein the hydrocarbon polymer chain corresponds to general formula (IIIa) wherein Z is a carbon or oxygen atom, wherein n is between 2 and 50, preferably between 3 and 30 and even more preferentially between 5 and 25, and wherein A is a radical corresponding to formula (A2) or to a related radical of a TDI trimer which comprises a number of isocyanate functions strictly greater than 1 and less than or equal to 2.2.

According to another embodiment, the polymerizable plasticizer has general formula (II), wherein the hydrocarbon polymer chain corresponds to general formula (IIIa) wherein Z is a carbon or oxygen atom, wherein n is between 2 and 50, preferably between 3 and 30 and even more preferentially between 5 and 25, and wherein A is a radical corresponding to one of the formulae (A3) and/or (A4) or to a related radical of a HDI trimer which comprises a number of isocyanate functions strictly greater than 1 and less than or equal to 2.2.

According to another embodiment, the polymerizable plasticizer has general formula (II), wherein the hydrocarbon polymer chain corresponds to general formula (IIIa) wherein Z is a carbon or oxygen atom, wherein n is between 2 and 50, preferably between 3 and 30 and even more preferentially between 5 and 25, and wherein A is a radical corresponding to formula (A5) or to a related radical of an IPDI trimer which comprises a number of isocyanate functions strictly greater than 1 and less than or equal to 2.2.

According to a particularly preferred embodiment, the polymerizable plasticizer has general formula (II), wherein the hydrocarbon polymer chain corresponds to general formula (IIIa) wherein Z is a carbon or oxygen atom, wherein n is between 2 and 50, preferably between 3 and 30 and even more preferentially between 5 and 25, and wherein A is a polymer chain (originating from a polymeric MDI) corresponding to formula (A1) which comprises a number of isocyanate functions strictly greater than 1 and less than or equal to 2.2.

According to a particular embodiment, the polymerizable plasticizer has general formula (II), wherein the hydrocarbon polymer chain corresponds to general formula (IIIb) wherein n is between 2 and 50, preferably between 3 and 30 and even more preferentially between 5 and 25.

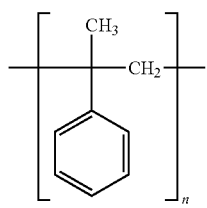

(IIIb)

According to a particular embodiment, the polymerizable plasticizer has general formula (II), wherein the hydrocarbon polymer chain corresponds to general formula (IIIb), wherein n is between 2 and 50, preferably between 3 and 30 and even more preferentially between 5 and 25, and wherein A is a radical corresponding to formula (A2) or to a related radical of a TDI trimer which comprises a number of isocyanate functions strictly greater than 1 and less than or equal to 2.2.

According to another embodiment, the polymerizable plasticizer has general formula (II), wherein the hydrocarbon polymer chain corresponds to general formula (IIIb), wherein n is between 2 and 50, preferably between 3 and 30 and even more preferentially between 5 and 25, and wherein A is a radical corresponding to one of the formulae (A3) and/or (A4) or to a related radical of a HDI trimer which comprises a number of isocyanate functions strictly greater than 1 and less than or equal to 2.2.

According to another embodiment, the polymerizable plasticizer has general formula (II), wherein the hydrocarbon polymer chain corresponds to general formula (IIIb), wherein n is between 2 and 50, preferably between 3 and 30 and even more preferentially between 5 and 25, and wherein A is a radical corresponding to formula (A5) or to a related radical of an IPDI trimer which comprises a number of isocyanate functions strictly greater than 1 and less than or equal to 2.2.

According to a particularly preferred embodiment, the polymerizable plasticizer has general formula (II), wherein the hydrocarbon polymer chain corresponds to general formula (IIIb), wherein n is between 2 and 50, preferably between 3 and 30 and even more preferentially between 5 and 25, and wherein A is a polymer chain (originating from a polymeric MDI) corresponding to formula (A1) which comprises a number of isocyanate functions strictly greater than 1 and less than or equal to 2.2.

Said polymerizable plasticizer according to the invention may be obtained by reaction between:
- an alcohol type compound containing a hydrocarbon chain comprising and/or being substituted with an aromatic ring and/or an aliphatic ring and/or the hydrocarbon chain of the alcohol type compound being substituted with at least two hydrocarbon chains which may comprise an unsaturation and wherein said alcohol type compound has an —OH number between 0.8% and 2.5%, preferably between 1.3% and 2.4% and even more preferentially between 1.4% and 1.7% by weight relative to the weight of said compound; and
- a polyisocyanate comprising 2.1 to 3.2 isocyanate functions and preferably 2.5 to 3.1 isocyanate functions.

In general, the alcohol type compound is a resin bearing only one alcohol function, i.e. a monohydroxylated resin also known as a monoalcohol, preferably a phenolic monohydroxylated resin also known as a phenolic monoalcohol.

Examples of monohydroxylated resins that may be used include terpenic resins such as α-pinene, β-pinene, dipentene, D-limonene and turpentine. Examples of phenolic monohydroxylated resins that may be used include those described in Ullmanns Encyklopädie der technischen Chemie, 4th edition, vol. 12, pages 539 to 545 (Verlag Chemie, Weinheim 1976); Kirk-Othmer, Encyclopedia of Chemical Technology, 3rd edition, vol. 12, pages 852 to 869 (John Wiley & Sons, New York, 1980); and Encyclopedia of Polymer Science and Engineering, vol. 7, pages 758 to 782 (John Wiley & Sons, New York, 1987).

Examples of preferred phenolic monoalcohols comprise phenolic α-methylstyrene resins and phenolic coumarone resins.

An example of an alcohol type compound is a phenolic monoalcohol of general formula (IV):

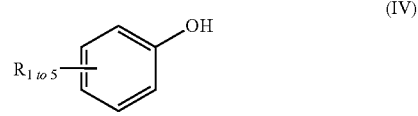

wherein $R_{1\ to\ 5}$ are each independently:
halogen,
alkyl,
haloalkyl,
cycloalkyl,
aryl,
alkoxy,
arylalkyl,
heteroaryl,
monounsaturated or polyunsaturated hydrocarbon chain;
and wherein $R_1$ to 5 do not contain any hydroxyl functions or any isocyanate functions;
and wherein at least one from among $R_{1\ to\ 5}$ represents a hydrocarbon polymer chain comprising and/or being substituted with at least one repeating unit:
alkyl,
aryl,
arylalkyl,
arylcycloalkyl,
arylheterocycloalkyl,
heteroaryl,
heteroarylalkyl,
heteroarylcycloalkyl,
heteroarylheterocycloalkyl,
hydrocarbyl with at least one unsaturation.

Another example of a phenolic monoalcohol has general formula (V) wherein each R independently represents an arylheterocycloalkyl and/or an arylcycloalkyl comprising 9 to 10 carbons and/or a unit derived from the polymerization of α-methylstyrene.

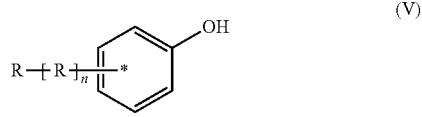

A particular example of a phenolic resin is a resin of general formula (V) wherein each R independently represents benzofuranyl or indenyl.

A preferred example of a phenolic resin is a resin according to general formula (V) wherein each R represents a unit derived from the polymerization of α-methylstyrene.

A preferred example of a phenolic monoalcohol is a coumarone resin substituted with a phenol at one end, such as Novares® CA 100 resin or Novares® CA 120 resin sold by RUtgers or an α-methylstyrene resin substituted with a phenol at one end, such as Nevoxy® EPX-L5 resin sold by Neville, Novares® LA 300 resin (CAS 68512-30-1) sold by RUtgers or Epodil® L resin sold by Air Products or a phenolic aromatic hydrocarbon resin such as Novares® LC 15 resin or Novares® LC 20 resin sold by Rütgers.

According to a preferred embodiment, the phenolic monoalcohol is Novares® LA 300 resin (CAS 68512-30-1).

The polyisocyanate may be an aromatic, aliphatic or cycloaliphatic polyisocyanate.

Said polyisocyanate may be chosen from the group comprising a TDI trimer, a polymeric MDI, a HDI trimer and an IPDI trimer, and mixtures thereof.

An example of an aromatic polyisocyanate that may be used is a polymeric diphenylmethane diisocyanate (MDI) containing 2.7 isocyanate functions, such as Suprasec® 5025 sold by Huntsman.

An example of an aliphatic polyisocyanate that may be used is a HDI trimer containing approximately 3 isocyanate functions, such as Desmodur® N3300 or Desmodur® N100 sold by Bayer.

Polyurethane Resin Composition

A second object of the invention is a polyurethane resin composition, preferably a stable, liquid one-component polyurethane resin composition comprising, besides a prepolymer, the previously described polymerizable plasticizer. According to a particular embodiment, the polyurethane resin composition comprises the previously described polymerizable plasticizer, a prepolymer, and optionally a solvent, a catalyst, liquid fillers and/or solid fillers.

Preferably, the polyurethane resin composition according to the invention is not a polyurethane foam composition. As a result, according to a particular embodiment, the composition according to the invention will not be mixed with water to polymerize and give a polyurethane foam. Similarly, the composition according to the invention is not intended to be mixed with a blowing agent such as a gas, for example propane, butane, isobutane, carbon dioxide, carbon monoxide or dimethyl ether to form a polyurethane foam.

The prepolymers are commercial products but may also be synthesized before preparing the polyurethane resin composition. Conventionally, the prepolymers are formed by reaction between:
- a polyol containing between 1.5 and 3 OH functions and having a molecular weight between 900 and 3,000 g/mol, preferably between 1,000 and 2,800 g/mol and more preferentially between 1,500 and 2,500 g/mol; and
- a diisocyanate and/or a polyisocyanate containing between 1.6 and 3 NCO functions;
in a ratio such that the number of NCO functions of the polyisocyanate relative to the number of OH functions of the polyol is from 1.5 to 2.5 approximately.

The polyol used to form the prepolymer may be a polyether, polyester, polybutadiene or polycarbonate type polyol and mixtures thereof.

The polyether type polyol may be a polypropylene glycol, a polyethylene glycol, a polypropylene glycol glycerol triol, a polyethylene glycol glycerol triol, or a polytetrahydrofuran.

The polyester type polyol may be a polycaprolactone, a polyester of fatty acid dimers comprising 34 to 36 carbon atoms, a polyadipate polyester or a polyphthalate polyester.

The polycarbonate polyol may be a 1,6-hexanediol polycarbonate.

Preferably, the polyol containing between 1.5 and 3 OH functions and having a molecular weight between 900 and 3,000 g/mol used to form the prepolymer is a polytetrahydrofuran, a 1,6-hexanediol polycarbonate, a polyester of fatty acid dimers comprising 34 to 36 carbon atoms, a polycaprolactone or a hydroxylated polybutadiene.

The diisocyanate and/or polyisocyanate used to form the prepolymer may be MDI, a polymeric MDI, TDI, a TDI trimer, HDI, a HDI trimer, IPDI, an IPDI trimer, and mixtures thereof.

Preferably, the diisocyanate and/or the polyisocyanate used to form the prepolymer is MDI, a polymeric MDI, TDI, a TDI trimer, and mixtures thereof.

The fillers that may be introduced into the present composition are especially liquid fillers that are exogenous plasticizers, natural or synthetic bitumens or a liquid bituminous mixture also known as a "cut-back", and solid fillers such as pigments, calcium carbonate, titanium oxide or the like.

The catalyst that may be introduced into the present composition makes it possible to accelerate the polymerization of the composition. The catalysts that may be introduced in the composition according to the invention are catalysts conventionally used in polyurethane compositions. Examples that may be used include organometallic catalysts based on bismuth, vanadium or tin, such as dibutyltin dilaurate, and tertiary amines, such as Jeffcat® DMDLS sold by Huntsman.

The present composition contains little or no solvent. The term "little solvent" means a solvent content of less than 10%, preferably less than 5% and more preferentially less than 2% by weight relative to the weight of the composition. Indeed, the polymerizable plasticizer object of the invention has high viscosity-lowering power. Thus, the compositions made with said polymerizable plasticizer are liquid even though they contain little or no solvent. This advantage is a considerable economic and ecological bonus.

According to a particularly preferred embodiment, the compositions do not contain any solvent at all.

A composition according to the invention comprises:
- from 30% to 90%, preferably from 35% to 75% and even more preferentially from 40% to 60% by weight of a prepolymer relative to the weight of the composition;
- from 10% to 70%, preferably from 15% to 50% and even more preferentially from 20% to 45% by weight of polymerizable plasticizer relative to the weight of the composition;
- from 0 to 20%, preferably from 2% to 15% and even more preferentially from 5% to 10% by weight of a solid filler relative to the weight of the composition;
- from 0 to 60%, preferably from 5% to 40% and even more preferentially from 10% to 35% by weight of a liquid filler relative to the weight of the composition;
- from 0 to 10%, preferably from 0 to 5% and even more preferentially from 0 to 2% by weight of solvent relative to the weight of the composition;
- from 0 to 5%, preferably from 0.5% to 3% and even more preferentially from 1.2% to 2% by weight of catalyst relative to the weight of the composition.

Methods

An object of the present invention is also a method for reducing the amount of solvent in polyurethane resin compositions or in bituminous polyurethane resin compositions, which are preferably one-component compositions. This method consists in adding the polymerizable plasticizer according to the invention to the constituents of a standard polyurethane resin composition or bituminous polyurethane resin composition, in replacement of some or all of the solvent and/or exogenous plasticizers conventionally used.

The method according to the invention makes it possible to lower the solvent content below 10%, preferably below 5% and even more preferentially below 2%. In a preferred embodiment, it makes it possible to eliminate all of the solvent.

A subject of the present invention is also a method for reducing, or even eliminating, the amount of exogenous plasticizer in polyurethane resin compositions or in bituminous polyurethane resin compositions, which are preferably one-component compositions. This method consists in adding the polymerizable plasticizer according to the invention to the constituents of a standard polyurethane resin composition or bituminous polyurethane resin composition, in replacement for some or all of the exogenous plasticizer(s) conventionally used.

The presence of the polymerizable plasticizer according to the invention also makes it possible to incorporate natural or synthetic bitumens into a polyurethane composition which does not contain any compatibilizers such as exogenous plasticizers, and makes it possible to obtain a stable liquid composition.

Use

Another object of the invention is the use of the previously described polymerizable plasticizer in polyurethane resin compositions, preferably in stable one-component polyurethane resin compositions. The use of the polymerizable plasticizer according to the invention makes it possible to lower the viscosity of the composition and improves the compatibility between the hydrocarbon fillers and the prepolymers, which makes it possible to obtain a stable composition.

The invention also relates to the use of the composition according to the invention for producing a coating, especially a waterproof coating, which has good mechanical strength, is resistant to UV, to oxidation, to aging, to water and to chemical attack, and which does not have any surface defects or adhesion defects (bubbles, swelling or exudation). Such coatings may be traffic-bearing and are particularly suitable for use in an unprotected exterior medium as waterproof coatings. The obtained coatings have an entirely satisfactory water uptake, i.e. less than 8% after and 28 days of immersion in water at 20° C. The coatings obtained by the use of the composition according to the invention can cover horizontal, oblique, vertical or rough surfaces and/or surfaces comprising singular points.

The non-bituminous polyurethane resin compositions are preferentially used for waterproofing exterior traffic-bearing horizontal surfaces, such as balconies, stadium terraces, car parks, building courtyards, etc.

The bituminous polyurethane resin compositions are preferentially used for making flashings, i.e. for making a waterproof coating between a bituminous surface and a vertical wall or a singular point, or for renovating roofs.

The invention will be described in greater detail with the aid of the following examples, which are given for purely illustrative purposes.

EXAMPLES

In the examples, the parts are expressed on a weight basis. The viscosities are measured using a Brookfield viscometer, spindle 5 or 6, speed 20 rpm at 23° C., less than one week after manufacturing the product or the composition.

In the examples, the following commercial products and acronyms are used:

Novares® LA 300: phenol-terminated α-methylstyrene resin (CAS 68512-30-1) with an —OH number between 1.7 and 2.2 sold by Rutgers.

Suprasec® 5025: a polymeric MDI containing 2.7 isocyanate functions, sold by Huntsman.

Suprasec® 2385: modified MDI containing 2 isocyanate functions sold by Huntsman.

Desmodur® N3300: HDI trimer containing 3 isocyanate functions sold by Bayer.

Desmodur® L 75: TDI trimer containing 3 isocyanate functions sold by Bayer.

Desmodur® Z 4470: IPDI trimer containing 3 isocyanate functions, dissolved in 70% strength butyl acetate or naptha solvent, sold by Bayer.

Voranol® 2000: polypropylene glycol with a molecular weight of 2,000 g/mol (CAS 025322-69-4) sold by Dow Chemical.

Voranol® CP 450: polypropylene glycol glycerol triol (CAS 025791-96-2) with a molecular weight of 450 g/mol sold by Dow Chemical.

Terathane® 2000: polytetrahydrofuran with a molecular weight of 2,000 g/mol (CAS 24979-97-3) sold by Dupont.

Voranate® T80: TDI sold by Dow Chemical.

Ruetasolv® Di: diisopropylnaphthalene plasticizing aromatic oil sold by Rutgers.

Incozol® LV: bis-oxazolidine comprising a carbonate group (CAS 145899-78-1) sold by Incorez.

PCP 1000: polycaprolactone containing 2 OH functions and having a molecular weight of 1,000 g/mol sold by Solvay.

Example 1

Preparation of a Polymerizable Plasticizer

The following constituents are mixed in a reactor:
100 parts of Novares® LA 300 resin,
25 parts of Suprasec® 5025.

The mixture is heated for at least 12 hours at about 100° C.

A polymerizable plasticizer with a viscosity of 1,300 centipoises and a molecular weight of 1,600 g/mol is obtained.

Example 2

Preparation of a Polymerizable Plasticizer

The following constituents are mixed in a reactor:
100 parts of Novares® LA 300,
36 parts of Suprasec® 5025.

The mixture is heated for at least 12 hours at about 100° C.

A polymerizable plasticizer with a viscosity of 1,500 centipoises and a molecular weight of 1,300 g/mol is obtained.

Example 3

Preparation of a Polymerizable Plasticizer

The following constituents are mixed in a reactor:
100 parts of Novares® LA 300,
36 parts of Desmodura N3300.

The mixture is heated for at least 12 hours at about 100° C.

A polymerizable plasticizer with a viscosity of 9,000 centipoises and a molecular weight of 1,700 g/mol is obtained.

Example 4

Preparation of a Polymerizable Plasticizer

The process is performed as in example 2, the amounts being modified in the following manner:
  100 parts of Novares® LA 300,
  38 parts of Suprasec® 5025.
A polymerizable plasticizer with a viscosity of about 1,500 centipoises and a molecular weight of 2,200 g/mol is obtained.

Example 5

Preparation of a Polymerizable Plasticizer

The process is performed as in example 2, the amounts being modified in the following manner:
  100 parts of Novares® LA 300,
  60 parts of Desmodur® L75.
A polymerizable plasticizer with a viscosity of about 1,200 centipoises and a molecular weight of 1,659 g/mol is obtained.

Example 6

Preparation of a Polymerizable Plasticizer

The process is performed as in example 2, the amounts being modified in the following manner:
  100 parts of Novares® LA 300,
  60 parts of Desmodur® Z 4470.
A polymerizable plasticizer with a viscosity of about 700 centipoises and a molecular weight of 1,666 g/mol is obtained.

Example 7

Preparation of a Polymerizable Plasticizer

The process is performed as in example 2, the amounts being modified in the following manner:
  100 parts of Novares® LA 300,
  40 parts of Desmodur® N 3300.
A polymerizable plasticizer with a viscosity of about 2,500 centipoises and a molecular weight of 1,400 g/mol is obtained.

Example 8

Preparation of a Liquid Polyurethane Resin Composition (Comparative)

The following ingredients are mixed in a reactor so as to form the prepolymer:
  200 parts of Voranol® 2000,
  24 parts of Voranol® CP 450,
  60 parts of Voranate® T80.
The mixture is stirred at 80° C. for 2 hours and, after cooling to about 40° C., the following constituents are added:
  24 parts of xylene,
  150 parts of Ruetasolv® Di,
  200 parts of calcium carbonate as pulverulent filler.
The composition obtained has a Brookfield viscosity (spindle 5, speed 10) at 23° C. of 1,800 centipoises and is applied as an interior coating under tiling. This composition gives off a strong odor of solvent and the coating obtained shows substantial water absorption of about 17% and a lack of adhesion due to the use of plasticizing oil.

Example 9

Preparation of a Liquid Polyurethane Resin Composition Comprising the Polymerizable Plasticizer The following ingredients are mixed in a reactor so as to form the prepolymer:
  200 parts of Voranol® 2000,
  24 parts of Voranol® CP 450,
  60 parts of Voranate® T80.
The mixture is stirred at 80° C. for 2 hours and the following constituents are then added:
  200 parts of polymerizable plasticizer prepared according to example 4,
  200 parts of pulverulent filler.
A solvent-free liquid one-component composition which has a Brookfield viscosity (spindle 5, speed 10) at 23° C. of 4,500 centipoises is obtained. The composition is applied as an interior coating under tiling. The coating obtained shows water absorption reduced to about 7% and adheres perfectly to the concrete support.

The composition is stored for 4 months at 20° C. After 4 months, the composition rapidly becomes homogeneous when it is mixed with a stick, and no phase separation is observed.

Example 10

Preparation of a Liquid Polyurethane Resin Composition Comprising the Polymerizable Plasticizer The following ingredients are mixed in a reactor so as to form an MDI masked with hexanol:
  37 parts of Suprasec® 5025,
  10.2 parts of hexanol.
The hexanol is gradually added to the MDI so as to keep the temperature of the reaction mixture below 60° C. When the addition of hexanol is complete, the mixture is left to return to room temperature.

The following ingredients are mixed in a reactor so as to form the prepolymer:
  24 parts of Terathane® 2000,
  6 parts of Suprasec® 2385,
  6 parts of MDI masked with hexanol, synthesized above,
  9 parts of Ruetasolv® Di,
  0.084 part of benzoyl chloride.
The reaction mixture is stirred at 400 rpm for 3 hours at 50° C.

The following ingredients are mixed in a dispersion tank so as to form the polyurethane resin composition:
  48.3 parts of prepolymer synthesized above,
  38.7 parts of polymerizable plasticizer synthesized according to example 1,
  4.3 parts of gray pigment RAL 7040,
  5.9 parts of Incozol® LV,
  2.4 parts of methyltetrahydrophthalic anhydride,
  0.4 part of benzoyl chloride.
The mixture is stirred at room temperature at a speed of 600 rpm for 6 minutes.

A solvent-free liquid one-component composition which has a Brookfield viscosity (spindle 6, speed 20) at 23° C. of 14,000 centipoises is obtained. The composition is applied directly onto concrete as an interior coating under tiling. The coating obtained shows water absorption reduced to about 7% and adheres perfectly to the concrete support.

The composition is stored for 4 months at 20° C. After 4 months, the composition rapidly becomes homogeneous when it is mixed with a stick, and no phase separation is observed.

Example 11

Preparation of a Liquid Polyurethane Resin Composition Comprising the Polymerizable Plasticizer The following ingredients are mixed in a reactor so as to form the prepolymer:
540 parts of Voranate® T80,
90 parts of 1,4-butanediol,
1000 parts of PCP 1000,
45 parts of Voranol® CP 450,
120 parts of butyl acetate.
The mixture is stirred at 80° C. for 1 hour 30 minutes.
The following ingredients are mixed in a dispersion tank so as to form the polyurethane resin composition:
100 parts of prepolymer synthesized above,
50 parts of polymerizable plasticizer synthesized according to example 7,
10 parts of gray pigment RAL 7040,
14 parts of Incozol® LV,
1 part of methyltetrahydrophthalic anhydride.
The mixture is stirred at room temperature at a speed of 600 rpm for 6 minutes.

A liquid one-component composition with a low solvent content (4% solvent) which has a Brookfield viscosity (spindle 6, speed 20) at 23° C. of 6,000 centipoises is obtained. The composition is applied directly onto concrete in exterior use, for example on a balcony. The coating obtained shows water absorption reduced to about 7% and adheres perfectly to certain concrete supports.

The invention claimed is:

1. A polymerizable plasticizer containing a hydrocarbon chain, only one end of which bears more than one isocyanate function, said hydrocarbon chain comprising and/or being substituted with an aromatic ring and/or an aliphatic ring and said hydrocarbon chain being substituted with at least two hydrocarbon chains that comprise an unsaturation, and the number of isocyanate functions being strictly greater than 1 and less than or equal to 2.2.

2. The polymerizable plasticizer according to claim 1, having a viscosity between 400 and 14,000 centipoises.

3. The polymerizable plasticizer according to claim 1, having general formula (I):

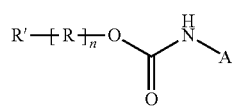

(I)

wherein each R independently represents a repeating unit which does not comprise any hydroxyl functions or any isocyanate functions and which is chosen from the group consisting of:
alkylene,
cycloalkylene,
arylene,
heteroarylene,
arylcycloalkylene,
arylheterocycloalkylene,
heteroarylalkylene,
heteroarylcycloalkylene, and
monounsaturated or polyunsaturated hydrocarbylene;
wherein R' represents a unit which does not comprise any hydroxyl functions or any isocyanate functions and which is chosen from the group consisting of:
alkyl,
cycloalkyl,
aryl,
heteroaryl,
arylcycloalkyl,
arylheterocycloalkyl,
heteroarylalkyl,
heteroarylcycloalkyl, and
monounsaturated or polyunsaturated hydrocarbyl;
and wherein n is between 2 and 50;
and wherein A is a group comprising a number of isocyanate functions strictly greater than 1 and less than or equal to 2.2, on condition that formula (I) comprises either at least one aromatic or aliphatic ring in at least one unit R or at least two alkylene units R substituted with an alkyl chain.

4. A polymerizable plasticizer having general formula (II)

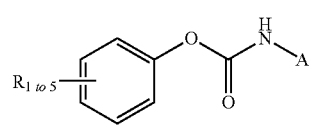

(II)

wherein substituents $R_{1\ to\ 5}$ are each independently:
halogen,
alkyl,
haloalkyl,
cycloalkyl,
aryl,
alkoxy,
arylalkyl,
heteroaryl, or
monounsaturated or polyunsaturated hydrocarbon chain;
and wherein $R_{1\ to\ 5}$ do not contain any hydroxyl functions or any isocyanate functions;
and wherein at least one from among $R_{1\ to\ 5}$ represents a hydrocarbon polymer chain comprising and/or being substituted with at least one repeating unit from the following:
alkyl,
aryl,
arylalkyl,
arylcycloalkyl,
arylheterocycloalkyl,
heteroaryl,
heteroarylalkyl,
heteroarylcycloalkyl,
heteroarylheterocycloalkyl, or
hydrocarbyl with at least one unsaturation;
and wherein A is a group comprising a number of isocyanate functions strictly greater than 1 and less than or equal to 2.2.

5. The polymerizable plasticizer according to claim 4, wherein the hydrocarbon polymer chain corresponds to general formula (IIIa) or (IIIb):

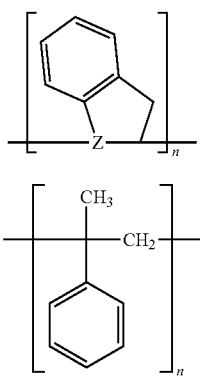

(IIIa)

(IIIb)

wherein Z is a carbon and/or oxygen atom; and wherein n is between 2 and 50.

6. The polymerizable plasticizer according to claim 5, wherein the hydrocarbon polymer chain corresponds to general formula (IIIb) wherein n is between 2 and 50 and wherein A is a polymer chain originating from polymeric MDI corresponding to formula (A1):

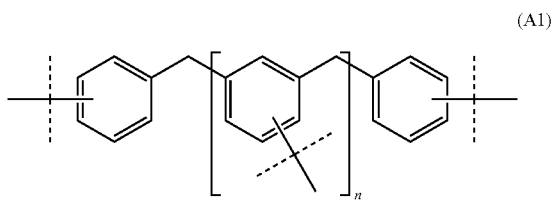

(A1)

and wherein A comprises a number of isocyanate functions strictly greater than 1 and less than or equal to 2.2.

7. The polymerizable plasticizer according to claim 5, characterized in that the hydrocarbon polymer chain corresponds to general formula (IIIb), wherein n is between 2 and 50 and wherein A is a radical corresponding to formula (A2):

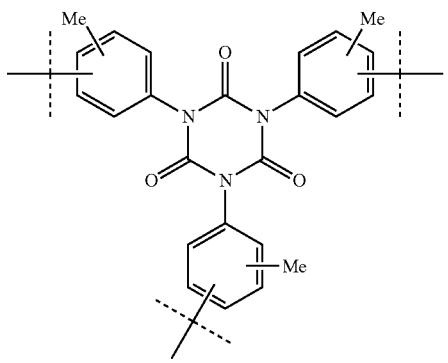

(A2)

and wherein A comprises a number of isocyanate functions strictly greater than 1 and less than or equal to 2.2.

8. The polymerizable plasticizer according to claim 4, wherein it is obtained by reaction between:
   an alcohol compound containing a hydrocarbon chain comprising and/or being substituted with an aromatic ring and/or an aliphatic ring and/or the hydrocarbon chain of the alcohol compound being substituted with at least two hydrocarbon chains that may comprise an unsaturation and wherein the alcohol compound has an —OH number between 0.8% and 2.5% by weight relative to the weight of said compound; and
   a polyisocyanate comprising 2.1 to 3.2 isocyanate functions.

9. The polymerizable plasticizer according to claim 8, wherein the alcohol compound is a phenolic monoalcohol of general formula (IV):

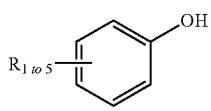

(IV)

wherein $R_{1\ to\ 5}$ are each independently:
   halogen,
   alkyl,
   haloalkyl,
   cycloalkyl,
   aryl,
   alkoxy,
   arylalkyl,
   heteroaryl, or
   optionally substituted monounsaturated or polyunsaturated hydrocarbon chain;
   and wherein $R_{1\ to}\ 5$ do not contain any hydroxyl functions or any isocyanate functions;
   and wherein at least one from among $R_{1\ to\ 5}$ represents a hydrocarbon polymer chain comprising and/or being substituted with at least one repeating unit from the following:
   alkyl,
   aryl,
   arylalkyl,
   arylcycloalkyl,
   arylheterocycloalkyl,
   heteroaryl,
   heteroarylalkyl,
   heteroarylcycloalkyl,
   heteroarylheterocycloalkyl, or
   hydrocarbyl with at least one unsaturation.

10. The polymerizable plasticizer according to claim 8, wherein the alcohol compound is a phenolic monoalcohol of general formula (V):

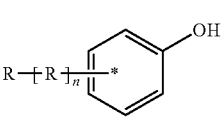

(V)

wherein each R represents a unit derived from the polymerization of α-methylstyrene.

11. The polymerizable plasticizer according to claim 8, wherein the alcohol compound is a coumarone resin substituted with a phenol at one end or an a-methylstyrene resin substituted with a phenol at one end.

12. A liquid polyurethane resin composition, comprising at least one polymerizable plasticizer according to claim 1, a prepolymer, and optionally a solvent, a catalyst, liquid fillers and/or solid fillers.

13. A method for reducing the amount of solvent in standard liquid polyurethane resin compositions or bituminous polyurethane resin compositions, comprising the addition of the polymerizable plasticizer according to claim 1 to said polyurethane composition in replacement for some or all of the solvent.

14. A method for reducing the amount of exogenous plasticizer in standard polyurethane resin compositions or bituminous polyurethane resin compositions, comprising the addition of the polymerizable plasticizer according to claim 1 to said polyurethane composition in replacement for some or all of the exogenous plasticizer.

15. The polymerizable plasticizer according to claim 1, wherein it is obtained by reaction between:
- an alcohol compound containing a hydrocarbon chain comprising and/or being substituted with an aromatic ring and/or an aliphatic ring and the hydrocarbon chain of the alcohol compound being substituted with at least two hydrocarbon chains that comprise an unsaturation and wherein the alcohol compound has an —OH number between 0.8% and 2.5% by weight relative to the weight of said compound; and
- a polyisocyanate comprising 2.1 to 3.2 isocyanate functions.

16. A liquid polyurethane resin composition, comprising at least one polymerizable plasticizer according to claim 4, a prepolymer, and optionally a solvent, a catalyst, liquid fillers and/or solid fillers.

17. A method for reducing the amount of solvent in standard liquid polyurethane resin compositions or bituminous polyurethane resin compositions, comprising the addition of the polymerizable plasticizer according to claim 4 to said polyurethane composition in replacement for some or all of the solvent.

18. A method for reducing the amount of exogenous plasticizer in standard polyurethane resin compositions or bituminous polyurethane resin compositions, comprising the addition of the polymerizable plasticizer according to claim 4 to said polyurethane composition in replacement for some or all of the exogenous plasticizer.

* * * * *